United States Patent [19]

Scotese et al.

[11] 4,301,281

[45] Nov. 17, 1981

[54] 7,8-DIHYDRO-2,5,8-TRISUBSTITUTED-7-OXO-PYRIDO[2,3-D]-PYRIMIDINE-6-CARBOXYLIC ACID AMIDES

[75] Inventors: Anthony C. Scotese, King of Prussia; Robert L. Morris, Devon; Arthur A. Santilli, Havertown, all of Pa.

[73] Assignee: American Home Products Corporation, New York, N.Y.

[21] Appl. No.: 125,620

[22] Filed: Feb. 28, 1980

Related U.S. Application Data

[63] Continuation-in-part of Ser. No. 31,256, Apr. 18, 1979, Pat. No. 4,215,216.

[51] Int. Cl.$^3$ ............................................. C07D 487/04
[52] U.S. Cl. ...................................... 544/80; 544/117; 544/279
[58] Field of Search ......................... 544/80, 117, 279

[56] References Cited

U.S. PATENT DOCUMENTS 4,128,649 12/1978 Goetz ................................. 424/256

4,134,981 1/1979 Althuis et al. ...................... 424/251

FOREIGN PATENT DOCUMENTS 851866 8/1977 Belgium .

OTHER PUBLICATIONS

Santilli et al., *J. Hetero. Chem.*, vol. 12, (1975), pp. 311–316.
Nishino et al., *Chem. Abstracts*, vol. 71, (1969), No. 49888a.
Blank et al., *Chem. Abstracts*, vol. 54, (1960), p. 5677(b).

*Primary Examiner*—John M. Ford
*Assistant Examiner*—R. W. Ramsuer
*Attorney, Agent, or Firm*—Richard K. Jackson

[57] ABSTRACT

7,8-Dihydro-2,5,8-trisubstituted-7-oxo-pyrido[2,3-d]pyrimidine-6-carboxylic acid amide derivatives are gastric anti-secretory agents for treatment of peptic ulcer disease and generally anti-allergic agents useful in the treatment of atopic immediate hypersensitivity reactions.

4 Claims, No Drawings

7,8-DIHYDRO-2,5,8-TRISUBSTITUTED-7-OXO-PYRIDO[2,3-D]-PYRIMIDINE-6-CARBOXYLIC ACID AMIDES

RELATED APPLICATIONS

This application is a continuation-in-part of Ser. No. 31,256, filed Apr. 18, 1979 now U.S. Pat. No. 4,215,216.

BRIEF DESCRIPTION OF THE INVENTION

In accordance with this invention there is provided a group of 7,8-dihydro-2,5,8-trisubstituted-7-oxopyrido[2,3-d]-pyrimidine-6-carboxylic acid derivatives which act as gastric antisecretory agents, by virtue of which they are useful in the treatment of peptic ulcer disease. Many of the compounds of this invention also exhibit anti-allergy activity, by virtue of which they are useful in the prophylactic suppression of allergic manifestations in warm-blooded animals.

As anti-secretory agents, the compounds of this invention reduce (1) total gastric volume, (2) hydrogen ion secretion, or (3) hydrogen ion concentration. The reduction of any one of these parameters aids in attenuating the general debilitating influence of a peptic ulcer in humans. The use of compounds exhibiting anti-secretory activity in the curative and/or prophylactic treatment of peptic ulcer disease is an established, beneficial procedure.

As anti-allergy agents, the compounds of this invention suppress the manifestations of an allergic response of the atopic immediate hypersensitivity type in warm-blooded, sensitized animals when administered prior to an allergic attack. Although the mechanism of action is not known, it is believed that the antiallergy agents of this invention function in the same manner as disodium cromoglycate (INTAL ®) to block reaction(s) within mast cells, thereby preventing the production and release of mediators such as Bradykinin, SRS-A (slow reacting substance-A), histamine and other unknown substances. The suppression of allergic manifestations is a desirable treatment in both human and domestic warm-blooded animals such as the mouse, rat, hamster, gerbil, dog, cat, sheep, goat horse and cow.

DETAILED DESCRIPTION OF THE INVENTION

The 7,8-dihydro-2,5,8-trisubstituted-7-oxopyrido[2,3-d]pyrimidine-6-carboxylic acid gastric antisecretory agents of this invention are depicted by the structural formula:

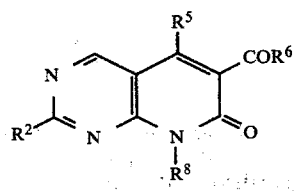

in which $R^2$ is hydrogen, hydroxy, alkyl of 1 to 6 carbon atoms, alkylthio of 1 to 6 carbon atoms, phenyl, 4-methoxyphenyl, 4-chlorophenyl, 1-pyrrolidinyl or methylphenylamino;

$R^5$ is hydroxy, alkylamino of 1 to 6 carbon atoms, 2-hydroxyethylamino, 2-alkoxyethylamino of 3 to 8 carbon atoms, dialkylamino wherein each alkyl group contains from 1 to 6 carbon atoms, 4-methyl-1-piperazinyl, 4-morpholinyl or 1-pyrrolidinyl when $R^2$ is other than alkylthio and $R^8$ is other than alkyl or —$NH_2$ when $R^8$ is other than alkyl;

$R^6$ is alkoxy of 1 to 6 carbon atoms, amino, mono- and di-alkylamino where each alkyl group contains from 1 to 6 carbon atoms, 2-hydroxyethylamino, 2-alkoxyethylamino of 3 to 8 carbon atoms or 2-(dialkylamino)ethylamino in which each alkyl group contains from 1 to 6 carbon atoms; and $R^8$ is hydrogen, alkyl of 1 to 6 carbon atoms, 2-alkoxyethyl of 3 to 6 carbon atoms, allyl, propargyl, phenyl, 4-methoxyphenyl, 4-chlorophenyl, benzyl, 4-methoxybenzyl, 4-chlorobenzyl, 4-(4-morpholinyl)phenyl or piperonyl;

or a pharmaceutically acceptable salt thereof.

The preferred anti-secretory agents based upon their ability to inhibit about fifty percent total acid output at a dose of 32 milligrams per kilogram i.d., are of the formula:

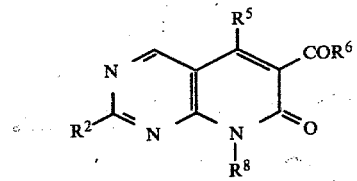

in which $R^2$ is phenyl, methylthio or 1-pyrrolidinyl;

$R^5$ is hydroxy, 2-methoxyethylamino or 1-pyrrolidinyl;

$R^6$ is ethoxy and $R^8$ is methyl, ethyl, propyl, allyl, 2-methoxyethyl, phenyl, piperonyl, 4-methoxybenzyl or benzyl.

The compounds of this invention which exhibit antiallergy activity present the structural formula:

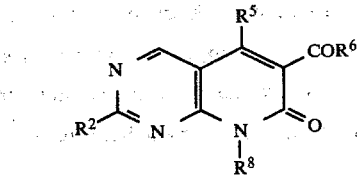

in which $R^2$ is hydrogen, hydroxy, alkyl of 1 to 6 carbon atoms, alkylthio of 1 to 6 carbon atoms, phenyl, 4-methoxyphenyl, 4-chlorophenyl, 1-pyrrolidinyl or methylphenylamino;

$R^5$ is hydroxy, alkylamino of 1 to 6 carbon atoms, dialkylamino wherein each alkyl group contains from 1 to 6 carbon atoms, 4-morpholinyl, 2-alkoxyethylamino of 3 to 8 carbon atoms or 2-hydroxyethylamino;

$R^6$ is alkoxy of 1 to 6 carbon atoms, 2-hydroxyethylamino, 2-alkoxyethylamino of 3 to 8 carbon atoms or 2-(dialkylamino)ethylamino in which each alkyl group contains from 1 to 6 carbon atoms; and $R^8$ is alkyl of 1 to 6 carbon atoms, 2-alkoxyethyl of 3 to 6 carbon atoms, allyl, propargyl, phenyl, 4-methoxyphenyl, 4-chlorophenyl, benzyl, 4-methoxybenzyl, 4-chlorobenzyl, 4-(4-morpholinyl)phenyl or piperonyl;

or a pharmaceutically acceptale salt thereof.

The compounds of this invention are produced by the following general technique:

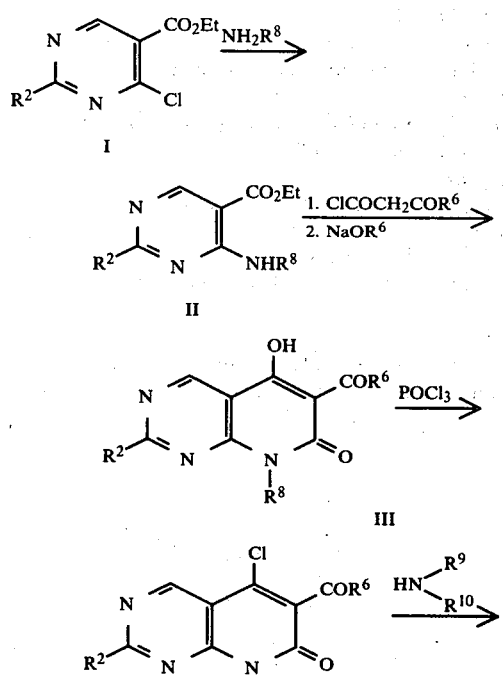

An alternate route involves hydrolysis of the ester of formula II, reaction with ethyl chloroformate followed by reaction with diethyl malonate and sodium ethoxide to produce the product of formula III, thusly:

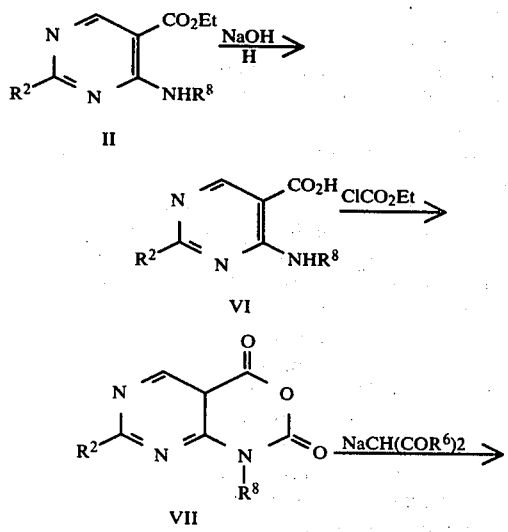

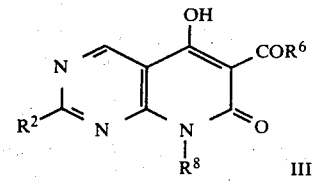

The substituent in 2-position of the 7,8-dihydro-2,5,8-trisubstituted-7-oxo-pyrido[2,3-d]pyrimidine-6-carboxylic acid derivatives of this invention may be converted to an amine or a hydroxy group by the following technique:

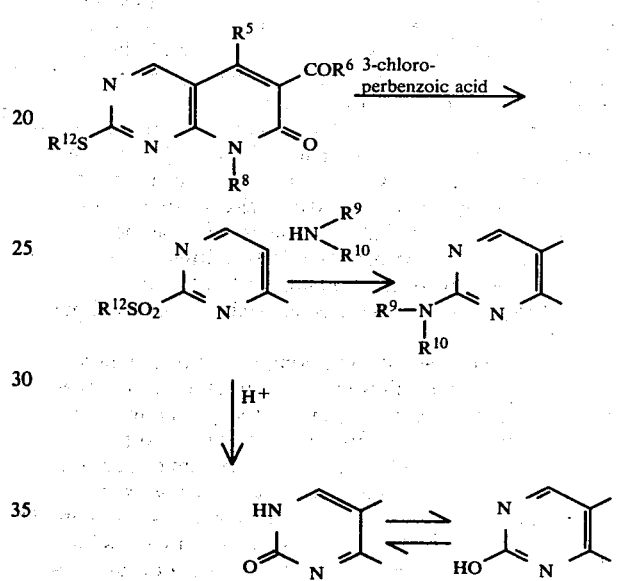

Compounds in which a primary amino group appears in 5-position may be produced by reaction of ethyl malonyl chloride with a 4-amino-5-cyano-2-substituted pyrimidine as follows:

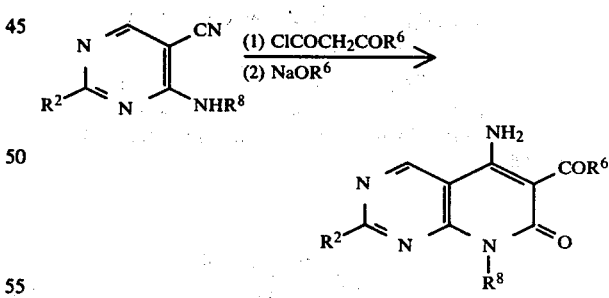

Alternatively, the 2-substituted aminonicotinonitrile may be reacted with the sodiom salt of a di-lower alkyl malonate to give directly on acidification the product of the preceding equation.

Conversion of the ester in 6-position to an amide —$CONR^9R^{10}$ where $R^9$ and $R^{10}$ independently represent hydrogen or alkyl of 1 to 6 carbon atoms procedes readily under known amidation conditions to provide a subgeneric compound embodiment of the invention. In each instance, the starting materials employed in the production of the compounds structurally depicted, supra, are either known compounds or are prepared by conventional methods. In the preceding equations, the substituents $R^2$, $R^5$ and $R^8$ are defined above, $R^6$ is alkoxy of 1 to 6 carbon atoms and $R^{12}$ is alkyl of 1 to 6 carbon atoms.

The pyrimido-oxazine-diones of formula VII, represent a compound intermediate aspect of this invention in that they are useful in production of the ultimate anti-secretory agents. The pyrimido-oxazine-diones present the structural formula:

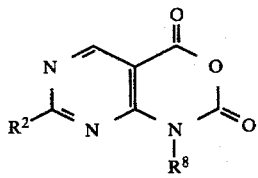

in which $R^2$ is hydrogen, hydroxy, alkyl of 1 to 6 carbon atoms, alkylthio of 1 to 6 carbon atoms, phenyl, 4-methoxyphenyl, 4-chlorophenyl, 1-pyrrolidinyl or methylphenylamino; and $R^8$ is hydrogen, alkyl of 1 to 6 carbon atoms, 2-alkoxyethyl of 3 to 6 carbon atoms, allyl, propargyl, phenyl, 4-methoxyphenyl, 4-chlorophenyl, benzyl, 4-methoxybenzyl, 4-chlorobenzyl, 4-(4-morpholinyl)phenyl or piperonyl.

The 5-chloro-pyrido-pyrimidines of formula IV constitute an additional compound intermediate aspect of the invention in that they are useful in the production of anti-secretory agents containing an amino substituent in 5-position. The 5-chloro-pyrido-pyrimidine intermediates present the structural formula:

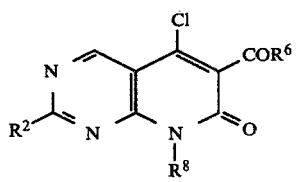

in which $R^2$ is hydrogen, hydroxy, alkyl of 1 to 6 carbon atoms, alkylthio of 1 to 6 carbon atoms, phenyl, 4-methoxyphenyl, 4-chlorophenyl, pyrrolidinyl or phenyl-methyl-amino;

$R^6$ is alkoxy of 1 to 6 carbon atoms; and $R^8$ is hydrogen, alkyl of 1 to 6 carbon atoms, alkoxyethyl of 3 to 6 carbon atoms, allyl, propargyl, phenyl, 4-methoxyphenyl, 4-chlorophenyl, benzyl, 4-methoxybenzyl, 4-chlorobenzyl, 4-(4-morpholinyl)phenyl or piperonyl.

An additional compound intermediate aspect of this invention resides in the 2-alkylsulfonyl pyrido-pyrimidines useful in the production of anti-secretory agents containing an amino or hydroxy substituent in 2-position. The 2-alkylsulfonyl pyridopyrimidines present the structural formula:

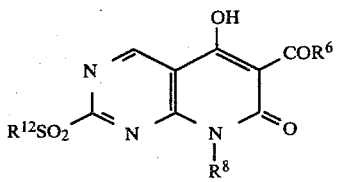

in which $R^6$ is alkoxy of 1 to 6 carbon atoms, amino, mono- or dialkylamino where each alkyl group contains from 1 to 6 carbon atoms, 2-hydroxyethylamino, 2-alkoxyethylamino of 3 to 8 carbon atoms or 2-(dialkylamino)ethylamino in which each alkyl group contains from 1 to 6 carbon atoms;

$R^8$ is hydrogen, alkyl of 1 to 6 carbon atoms, 2-alkoxyethyl of 3 to 6 carbon atoms, allyl, propargyl, phenyl, 4-methoxyphenyl, 4-chlorophenyl, benzyl, 4-methoxyphenyl, 4-chlorobenzyl or piperonyl; and $R^{12}$ is alkyl of 1 to 6 carbon atoms.

Each of the anti-secretory agents of this invention is active in the following scientifically recognized, standard test for gastric anti-secretory activity:

Male Charles River rats of Sprague-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally (i.d.). The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1 N NaOH. The calculated product of gastric volume (ml/4 hr) and acid concentration (mEq/L) estimates the total acid output (TAO, mEq/4 hr) over the four-hour test period. An analysis of variance is performed on these data to determine statistically significant ($p < 0.05$) deviation between control versus drug-treated groups.

Those compounds indicated above to be anti-allergy agents have demonstrated ability to relieve allergic manifestations when administered intraperitoneally to sensitized rats. Several of the compounds tested were found to be effective anti-allergy agents when administered orally to the sensitized animals.

The technique employed to establish the anti-allergic activity of the disclosed compounds is reported in Immunology, vol. 16, pp. 749–760 (1969) and involves four male Charles River rats (200–250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Twenty-four hours after the initial injections, the test compound is administered intraperitoneally or orally at a dosage level of 200 milligrams per kilogram host body weight. Five minutes later (unless otherwise indicated) one milliliter of a 0.5 percent solution of Evans blue dye and 8 milligrams of egg albumin is injected intravenously. After forty minutes, the animal is sacrificed and the bleb size on its back is measured. The mean bleb size for the animals administered the test compound is calculated and the percent inhibition is determined by comparison with the control animal.

Thus, the compounds disclosed herein are useful in the treatment of peptic ulcer disease and/or for symptomatic relief of atopic immediate hypersensitivity reactions. Where the two conditions occur simultaneously in the same patient, the compounds of this invention hold out the decided advantage of single compound therapeutic administration for both problems. Where the conditions occur separately, the second activity of the compounds is either inconsequential, as treatment of a nonsensitized animal with an anti-allergy agent, or of no deleterious effect that would be contraindicative of applicability of the treatment, as a decrease in total gastric acid output in an allergic animal does not preclude prophylactic treatment of the allergy. For either use, the dosage regimen will vary with the mode of administration, size and age of the subject treated as well as the severity of the dysfunction. Thus, administration of the compounds of this invention must be under the guidance and instruction of a physician, or in the case of treatment of domestic animals, a veterinarian.

The compounds of this invention may be administered by conventional oral or parenteral routes as solids, liquids or nebulized suspensions. Conventional adjuvants known to the art may be combined with the anti-secretory, anti-allergy agents of this invention to provide compositions and solutions for administrative purposes, although it is considered desirable and feasible to use neat or pure compounds without additives other than for the purpose of providing suitable pharmaceutically acceptable solution or liquid or vapor suspensions. Toward that end, those compounds which contain a basic amino substituent may be converted to pharmaceutically acceptable salts with such acids as hydrochloric, hydrobromic, sulfuric, phosphoric, methane sulfonic, nitric, p-toluene sulfonic, acetic, citric, maleic, succinic acid, and the like.

The following examples are presented to illustrate the production of representative compounds of this invention. After each example, the anti-secretory activity expressed as the percent inhibition of gastric total acid output at a dose of 32 milligrams per kilogram intraduodenal (i.d.) is presented for the exemplified compound. Likewise, the anti-allergy activity expressed as the percent inhibition of allergic response at the stated dose and route of administration, either intraperitoneal (i.p.) or oral (p.o.), is given for the exemplified compound where applicable.

EXAMPLE 1

8-Ethyl-7,8-dihydro-5-hydroxy-7-oxo-2-phenyl-pyrido[2,3-d]pyrimidine-6-carboxylic acid ethyl ester A solution of ethylamine gas (3.6 g.-0.04 mole) in cold ethanol was prepared and to this was added 2.2 g. (0.02 mole) of $Na_2CO_3$, followed by 10 g. (0.04 mole) of 4-chloro-2-phenyl-5-pyrimidine carboxylic acid ethyl ester. This was stirred in a stoppered flask overnight at room temperature. Then it was refluxed for one hour and filtered. The filtrate was stripped to dryness and scratched until crude solid began to form. This solid was recrystallized from hexane to give 6.0 g. of 4-ethylamino-2-phenyl-5-pyrimidine carboxylic acid ethyl ester—m.p. 43°–48° C.

Anal. calcd. for $C_{15}H_{17}N_3O_2$: C, 66.40; H, 6.32; N, 15.49. Found: C, 66.24; H, 6.15; N, 15.37.

To 9.2 g. (0.034 mole) of 4-ethylamino-2-phenyl-5-pyrimidine-carboxylic acid ethyl ester in diethyl ether was added to 2.6 g. (0.017 mole) of ethyl malonyl chloride and then stirred 3 hours at room temperature. The reaction was then filtered and the filtrate stripped to dryness. This residue was dissolved in ethanol and added to a solution of 0.78 g. of sodium (0.034 mole) in ethanol and stirred at room temperature for 10 minutes. Acidification with acetic acid followed by the slow addition of water resulted in the formation of a precipitate. The crude product was removed by filtration and recrystallized from hexane m.p. 175°–177° C.—to give 1.0 g. of the title product.

Anal. Calcd. for $C_{18}H_{17}N_3O_4$: C, 63.71; H, 5.05; N, 12.38. Found: C, 63.49; H, 5.12; N, 12.03.

Anti-secretory—45%

Anti-allergy—99%; 50 mg/kg. p.o.

EXAMPLE 2

8-Ethyl-7,8-dihydro-5-hydroxy-7-oxo-2-phenyl-pyrido[2,3-d]pyrimidine-6-carboxylic acid ethyl ester A solution of 20% NaOH (120 ml.) was added to 24.4 g. (0.09 mole) of 4-ethylamino-2-phenyl-5-pyrimidine carboxylic acid ethyl ester (prepared as in the first paragraph of Example 1) and was heated. 15 ml. of ethanol was added for solubility and this was refluxed 3 hours. When cooled and acidified with dilute acetic acid, a white solid formed which was collected on a filter and rinsed with 400 ml. of ethanol to give 18.4 g. of 4-ethylamino-2-phenyl-5-pyrimidine carboxylic acid. The compound was used directly in the next step without further purification, m.p. 262°–264° C. (dec).

Anal. calcd. for $C_{13}H_{13}N_3O_2$: C, 64.18; H, 5.38; N, 17.27. Found: C, 63.95; H, 5.05; N, 17.11.

A mixture of 200 ml. of ethyl chloroformate and 50 ml. of xylene was added to 18.4 g. (0.076 mole) of 4-ethylamino-2-phenyl-5-pyrimidine carboxylic acid and refluxed 27 hours. The reaction was then cooled and yielded 9 g. of 1-ethyl-7-phenyl-2H-pyrimido [4,5-d][1,3] oxazine-2,4(1H)-dione as a pink solid—m.p. 206°–211° C. The product was used directly in the next step without further purification.

Anal. calcd. for $C_{14}H_{11}N_3O_3$: C, 62.44; H, 4.12; N, 15.60. Found: C, 62.06; H, 4.15; N, 15.32.

To a 40 ml. solution of NaOEt (1.0 g. Na-0.042 mole) was added 6.8 g. (0.042 mole) of diethyl malonate and this is stirred 10 minutes, then stripped to dryness. Dimethylformamide was added until a solution formed and to this was added 5.7 g. (0.021 mole) of 1-ethyl-7-phenyl-2H-pyrimido[4,5-d][1,3]oxazine-2,4(1H)-dione and the mixture heated at reflux for 2 hours. The reaction was then cooled and poured into dilute HCl and the resulting precipitate filtered off and rinsed well with water. Recrystallization with hexane-ethyl acetate gave 5.1 g. of the title product—m.p. 177°–180° C.

Anal. calcd. for $C_{18}H_{17}N_3O_4$: C, 63.71; H, 5.05; N, 12.38. Found: C, 63.47; H, 5.10; N, 12.44.

Anti-secretory–45%

Anti-allergy–99%; 50 mg/kg. p.o.

EXAMPLE 3

8-Ethyl-7,8-dihydro-7-oxo-2-phenyl-5-(1-pyrrolidinyl)-pyrido[2,3-d]-pyrimidine-6-carboxylic acid ethyl ester 60 ml. OF POClhd 3 was added to 3.1 g. (0.009 mole) of 8-ethyl-7,8-dihydro-5-hydroxy-7-oxo-2-phenyl-pyrido[-b 2,3-d]pyrimidine-6-carboxylic acid ethyl ester (prepared by the method of Example 1) and this was refluxed 5 hours. The POCl$_3$ was then removed via a rotary evaporator and the residue was added to ice water. An off-white solid formed and was recrystallized from ethyl acetate to give 3 g. of 5-chloro-8-ethyl-7,8-dihydro-7-oxo-2-phenyl-pyrido[2,3-d]pyrimidine-6-carboxylic acid ethyl ester—m.p. 165°–168° C.

To 0.7 g. (0.002 mole) of 5-chloro-8-ethyl-7,8-dihydro-7-oxo-2-phenylpyrido[2,3-d]pyrimidine-6-carboxylic acid ethyl ester in ethanol was added 0.14 g. (0.002 mole) of pyrrolidine and 0.21 g. (0.002 mole) of sodium carbonate and this mixture was refluxed 3 hours. At that point, the solid inorganic material was filtered and the filtrate allowed to stand several days. Pale yellow crystals of the title compound formed which were removed by filtration—m.p. 149°–153° C.

Anal. calcd. for $C_{24}H_{22}N_4O_3$: C, 67.33; H, 6.16; N, 14.28. Found: C, 66.97; H, 5.93; N, 14.16.

Anti-secretory—71%

EXAMPLE 4

7,8-dihydro-8-ethyl-5-morpholino-7-oxo-2-phenyl-pyrido[2,3-d]pyrimidine carboxylic acid ethyl ester Four grams (0.011 mole) of 5-chloro-7,8-dihydro-8-ethyl-7-oxo-2-phenyl-pyrido[2,3-d]pyrimidine-6-carboxylic acid ethyl ester (prepared by the method of Example 3, first paragraph), 0.97 g. (0.011 mole) of morpholine and 1.2 g. (0.011 mole) of Na$_2$CO$_3$ were combined in 125 ml. of ethanol and heated at reflux for 4 hours. After heating, the reaction mixture was filtered and the filtrate chilled in ice. An orange solid formed which was collected on a filter. Recrystallization from ethanol gave 3.9 g. of product—m.p. 195°–197° C.

Anal. calcd. for $C_{22}H_{24}N_4O_4$: C, 64.69; H, 5.92; N, 13.72. Found: C, 64.42; H, 6.21; N, 13.81.

Anti-allergy—17%; 25 mg/kg. p.o.

EXAMPLE 5

7,8-dihydro-8-ethyl-5-(4-methyl-1-piperazinyl)-7-oxo-2-phenylpyrido[2,3-d]pyrimidine-6-carboxylic acid ethyl ester To 0.9 g. (0.0025 mole) of 5-chloro-7,8-dihydro-8-ethyl-7-oxo-2-phenylpyrido[2,3-d]pyrimidine-6-carboxylic acid ethyl ester (prepared by the method of Example 3, first paragraph) and 0.25 g. (0.0025 mole) of N-methyl piperazine in 40 ml. of ethanol was added 0.27 g. (0.0025 mole) of Na$_2$CO$_3$. The reaction mixture was refluxed for 3 hours after which time it was filtered and chilled in ice. The resulting precipitate was removed by filtration, and rinsed with diethyl ether, giving 0.7 g. of solid—m.p. 180°–185° C.

Anal. calcd. for $C_{23}H_{27}N_5O_3$: C, 65.53; H, 6.46; N, 16.62. Found: C, 65.61; H, 6.58; N, 16.59.

Anti-secretory—38%

EXAMPLE 6

5-diethylamino-7,8-dihydro-8-ethyl-7-oxo-2-phenyl-pyrido[2,3-d]pyrimidine-6-carboxylic acid ethyl ester Two grams (0.0056 mole) of 5-chloro-7,8-dihydro-8-ethyl-7-oxo-2-phenylpyrido[2,3-d]pyrimidine-6-carboxylic acid ethyl ester (prepared by the method of Example 3, first paragraph) and 0.82 g. (0.011 mole) of diethylamine were added together in ethanol in an autoclave and heated on a steam bath for 2 hours. The reaction mixture was then filtered and the filtrate chilled in ice. The precipitate which formed was collected on a suction filter. Recrystallization from ethyl acetate gave 0.8 g. of product m.p. 110°–115° C.

Anal. calcd. for $C_{22}H_{26}N_4O_3$: C, 66.98; H, 6.64; N, 14.20. Found: C, 66.69; H, 6.74; N, 14.19.

Anti-secretory—29%

Anti-allergy—34%; 10 mg/kg i.p.

EXAMPLE 7

7,8-dihydro-5-hydroxy-7-oxo-2-phenyl-8-propyl-pyrido[2,3-d]pyrimidine-6-carboxylic acid ethyl ester A mixture of 23.3 g. (0.09 mole) of 4-chloro-2-phenyl-5-pyrimidine carboxylic acid ethyl ester and 10.5 g. (0.18 mole) of propylamine in 700 ml. of ethanol was refluxed for 3 hours. Then the volume was concentrated to 100 ml. and chilled. A white solid formed and was filtered off and rinsed with petroleum ether to give 22.4 g. of 4-propylamino-2-phenyl-5-pyrimidine carboxylic acid ethyl ester—m.p. 45°–46° C.

To 17.3 g. (0.06 mole) of 4-propylamino-2-phenyl-5-carboxylic acid ethyl ester in diethyl ether was added 4.6 g. (0.03 mole) of ethyl malonyl chloride and then stirred 3½ hours at room temperature. The reaction was then filtered and the filtrate stripped to dryness. The residue was dissolved in ethanol and added to a solution of 1.4 g. (0.06 mole) of sodium in ethanol and stirred 15 minutes at room temperature. Water and a little ethanol was added to form a clear solution which was then acidified with HCl carefully to precipitate the title compound. The crude product was filtered and recrystallized from ethyl acetate to give 0.6 g. of solid with the m.p. 162°–164° C.

Anal. calcd. for $C_{19}H_{19}N_3O_4$: C, 64.58; H, 5.42; N, 11.89. Found: C, 64.57; H, 5.32; N, 11.97.

Anti-secretory—69%

Anti-allergy—77%; 10 mg/kg p.o.

EXAMPLE 8

7,8-dihydro-5-hydroxy-7-oxo-2-phenyl-8-propyl-pyrido[2,3-d]pyrimidine-6-carboxylic acid ethyl ester 60 ml. of 20% NaOH was added to 9.8 g. (0.034 mole) of 4-propylamino-2-phenyl-5-pyrimidine carboxylic acid ethyl ester (prepared as in paragraph 1 of Example 7) and refluxed 3.5 hours. The cooled reaction was acidified with dilute acetic acid and a white solid was filtered off. This product was recrystallized from ethanol—m.p. 228°–230° C. (dec.). There was obtained 6.5 g. of 4-propylamino-2-phenyl-5-pyrimidine carboxylic acid which was used directly in the next step without further purification.

To 100 ml. of ethyl chloroformate and 25 ml. of xylene was added 6.3 g. (0.024 mole) of 4-propylamino-2-phenyl-5-pyrimidine carboxylic acid and refluxed 20 hours. Upon cooling and scratching a yellow solid formed which was filtered and rinsed with petroleum ether to give 1.15 g. of 1-propyl-7-phenyl-2H-pyrimido[4,5-d][1,3]oxazine-2,4(1H)-dione—m.p. 179°–181° C. The product was used in the next step without further purification.

Anal. calcd. for $C_{15}H_{13}N_3O_3$: C, 63.60; H, 4.62; N, 14.83. Found: C, 63.58; H, 4.64; N, 14.59.

50 ml. of NaOEt (0.24 g.-0.011 mole) was added to 1.7 g. (0.011 mole) of ethyl malonate and stirred 10 minutes, then evaporated to dryness. DMF was added until a solution formed and 1.5 g. (0.005 mole) of 7-phenyl-1-propyl-2H-pyrimido[4,5-d][1,3]oxazine-2,4(1H)-dione was added and the mixture refluxed 2 hours. The chilled reaction was poured into dilute HCl and the resulting precipitate filtered off and rinsed with water. Recrystallization from ethyl acetate gave 1.5 g. of the title compound—m.p. 164°-167° C.

Anal. calcd. for $C_{19}H_{19}N_3O_4$: C, 64.58; H, 5.42; N, 11.89. Found: C, 64.62; H, 5.37; N, 11.94.

Anti-secretory—69%

Anti-allergy—77%; 10 mg/kg p.o.

EXAMPLE 9

7,8-dihydro-5-hydroxy-8-(2-methoxyethyl)-7-oxo-2-phenylpyrido[2,3-d]pyrimidine-6-carboxylic acid ethyl ester A mixture of 15.5 g. (0.059 mole) of 4-chloro-2-phenyl-5-pyrimidine carboxylic acid ethyl ester and 8.9 g. (0.118 mole) of 2-methoxyethylamine in 500 ml. of ethanol was refluxed 4.5 hours. The solution was then concentrated to 100 ml. and chilled. A white solid formed and was filtered off and rinsed with ethanol to give 14.2 g. of 4-(2-methoxyethylamino)-2-phenyl-5-pyrimidine carboxylic acid ethyl ester with—m.p. 67°-74° C. Product was used in the next step without further purification.

Anal. calcd. for $C_{16}H_{19}N_3O_3$: C, 63.77; H, 6.36; N, 13.94. Found: C, 63.60; H, 6.44; N, 13.89.

To 14.2 g. (0.047 mole) of 4-(2-methoxyethylamino)-2-phenyl-5-carboxylic acid ethyl ester in ether was added 3.55 g. (0.024 mole) of ethyl malonyl chloride and then this mixture was stirred at room temperature for 4 hours. The reaction was filtered and the filtrate stripped to dryness. The residue was dissolved in ethanol and added to a solution of 1.08 g. (0.047 mole) of sodium in ethanol and stirred 20 minutes at room temperature. A little water and ethanol was added and the mixture was acidified with dilute HCl. After chilling the solution in ice, a white solid was formed which was filtered, rinsed with water and dried in a vacuum oven to give 0.45 g. of a solid with the m.p. 166°-168° C.

Anal. calcd. for $C_{19}H_{19}N_3O_5$: C, 61.78; H, 5.18; N, 11.38. Found: C, 61.67; H, 5.40; N, 11.04.

Anti-secretory—75%

Anti-allergy—100%; 100 mg/kg i.p.

EXAMPLE 10

7,8-dihydro-5-hydroxy-8-(2-methoxyethyl)-7-oxo-2-phenylpyrido[2,3-d]pyrimidine-6-carboxylic acid ethyl ester 60 ml. of 20% NaOH and 10 ml. of ethanol was added to 7.3 g. (0.024 mole) 4-(2-methoxyethylamino)-2-phenyl-5-pyrimidine carboxylic acid ethyl ester (prepared as in paragraph 1 of Example 9) and refluxed 3 hours. The reaction was then cooled, acidified with dilute acetic acid and filtered to removed the white solid. Recrystallization from ethanol gave 5.5 g. of 4.(2-methoxyethylamino)-2-phenyl-5-pyrimidine carboxylic acid with m.p. 220°-225° C.

Anal. calcd. for $C_{14}H_{15}N_3O_3$: C, 61.53; H, 5.53; N, 15.38. Found: C, 61.37; H, 5.48; N, 15.25.

100 ml. of ethyl chloroformate and 25 ml. of xylene were added to 5.5 g. (0.02 mole) of 4-(2-methoxyethylamine)-2-phenyl-5-pyrimidine carboxylic acid and refluxed 21 hours. When chilled, the reaction gave up a white solid which was collected by filtration and rinsed with petroleum ether to give 3.2 g. of 1-(2-methoxyethyl)-7-phenyl-2H-pyrimido[4,5-d][1,3]oxazine-2,4(1H)-dione—m.p. 172°-174° C. This compound was used in the next step without further purification.

Anal. calcd. for $C_{15}H_{13}N_3O_4$: C, 60.20; H, 4.38; N, 14.04. Found: C, 60.05; H, 4.38; N, 13.90.

50 ml. of NaOEt (0.5 g. Na—0.021 mole) was added to 3.4 g. (0.021 mole) of ethyl malonate and stirred 10 minutes, then evaporated to dryness. DMF was added until a solution was achieved and then 3.2 g. (0.011 mole) of 1-(2-methoxyethyl)-7-phenyl-2H-pyrimido[4,5-d][1,3]oxazine-2,4(1H)-dione was added and this mixture refluxed 2 hours. The chilled reaction was poured into dilute HCl and the ensuing precipitate filtered off and rinsed with water. Recrystallization from ethyl acetate gave 3.5 g. of the title product—m.p. 178°-179° C.

Anal. calcd. for $C_{19}H_{19}N_3O_5$: C, 61.78; H, 5.18; N, 11.38. Found: C, 61.90; H, 5.20; N, 11.35.

Anti-secretory—75%

Anti-allergy—100%; 100 mg/kg i.p.

EXAMPLE 11

7,8-dihydro-5-hydroxy-7-oxo-2-phenyl-8-(2-propenyl)-pyrido[2,3-d]pyrimidine-6-carboxylic acid ethyl ester A mixture of 5 g. (0.019 mole) of 4-chloro-2-phenyl-5-pyrimidine carboxylic acid ethyl ester and 2.2 g. (0.038 mole) of allylamine in 150 ml. of ethanol was refluxed 3 hours. At this point, the solution was concentrated to 30 ml. and chilled. A yellow crystalline solid formed and was filtered off to give 4-(2-propenylamino)-2-phenyl-5-pyrimidine carboxylic acid ethyl ester—m.p. 49°-54° C. This compound was used in the next step directly without further purification.

To 16.3 g. (0.057 mole) of 4-(2-propenylamino)-2-phenyl-5-pyrimidine carboxylic acid ethyl ester in diethyl ether was added 4.3 g. (0.029 mole) of ethyl malonyl chloride and then stirred 3 hours at room temperature. The reaction was then filtered and stripped to dryness and the residue was added to a solution of 1.3 g. (0.057 mole) of Na in ethanol and stirred at room temperature for 10 minutes. Water was added until the reaction became clear and then acidified with HCl. This solution was chilled in ice and the resulting solid was removed by filtration. Recrystallization from ethyl acetate gave 0.55 g. of title product with m.p. 174°-175° C.

Anal Calcd. for $C_{19}H_{17}N_3O_4 \cdot \frac{1}{4}H_2O$: C, 64.22; H, 4.96; N, 11.81. Found: C, 64.29; H, 4.78; N, 11.90.

Anti-secretory—68%

Anti-allergy—87%; 50 mg/kg i.p.

EXAMPLE 12

7,8-dihydro-5-hydroxy-7-oxo-2-phenyl-8-(2-propenyl)-pyrido[2,3-d]pyrimidine-6-carboxylic acid ethyl ester 60 ml. of 20% NaOH was added to 5 g. (0.018 mole) of 4-(2-propenylamino)-2-phenyl-5-carboxylic acid ethyl ester and refluxed 4.5 hours. The reaction was then cooled, acidified with dilute acetic acid and then filtered to remove the white solid that had formed. Recrystallization from 95% ethanol gave 4.1 g. of 4-(2 propenylamino)-2-phenyl-5-pyrimidine carboxylic acid—m.p. 249° C. (dec.).

Anal. calcd. for $C_{14}H_{13}N_3O_2$: C, 65.87; H, 5.13; N, 16.46. Found: C, 65.49; H, 5.20; N, 16.55.

100 ml. of ethyl chloroformate and 25 ml. of xylene were added to 4.1 g. (0.016 mole) of 4-allylamino-2-phenyl-5-pyrimidine carboxylic acid and refluxed overnight. The insoluble material was removed by filtration. The filtrate was evaporated to dryness. The residue was recrystallized from ethanol to give 1.85 g. of 7-phenyl-1-(2-propenyl)-2H-pyrimido[4,5-d][1,3]oxazine2,4(1H)-dione—m.p. 188°–190° C.

Anal. Calcd. for $C_{15}H_{11}N_3O_3 \cdot \frac{1}{2}H_2O$: C, 61.64; H, 4.14; N, 14,38. Found: C, 61.26; H, 4.60; N, 14.08.

To a 50 ml. solution of NaOEt (0.3 g. Na–0.013 mole) was added 2.08 g. (0.013 mole) of diethyl malonate and this was stirred 10 minutes, then stripped to dryness. DMF was added to form a solution and then 1.85 g. (0.0065 mole) of 1-(2-propenyl)7-phenyl-2H-pyrimido[4,5-d][1,3]oxazine-2,4(1H)-dione was added and heated at reflux for 1.5 hours. When cool, the reaction was poured into dilute HCl and the resulting precipitate collected on a filter and rinsed with water. Recrystallization from ethyl acetate gave 1.0 g. of product—m.p. 177°–180° C.

Anal. Calcd. for $C_{19}H_{17}N_3O_4$: C, 64.95; H, 4.88; N, 11.96. Found: C, 64.71; H, 4.92; N, 11.89.

Anti-secretory—68%

Anti-allergy—87%; 50 mg/kg i.p.

EXAMPLE 13

7,8-dihydro-5-hydroxy-7-oxo-2-phenyl-8-(benzyl)-pyrido[2,3-d]pyrimidine-6-carboxylic acid ethyl ester A mixture of 15 g. (0.057 mole) of 4-chloro-2-phenyl-5-pyrimidine carboxylic acid ethyl ester, 6.12 g. (0.057 mole) of benzylamine and 3 g. (0.029 mole) of $Na_2CO_3$ in 200 ml. of ethanol was refluxed 4.5 hours. Then the reaction was cooled and filtered and a precipitate formed immediately in the filtrate. This solid was recrystallized from ethanol to give 8.3 g. of 4-benzylamino-2-phenyl-5-pyrimidine carboxylic acid ethyl ester with m.p. 112°–115° C.

Anal. calcd. for $C_{20}H_{19}N_3O_2$: C, 72.05; H, 5.74; N, 12.60. Found: C, 71.74; H, 5.71; N, 12.59.

To 11.0 g. (0.033 mole) of 4-benzylamino-2-phenyl-5-carboxylic acid ethyl ester in diethyl ether was added 2.5 g. (0.016 mole) of ethyl malonyl chloride and then stirred 3 hours at room temperature. The reaction was then filtered and the filtrate stripped to dryness. This residue was then dissolved in ethanol to which was then added a solution of 0.76 g. of sodium (0.033 mole) in ethanol. The reaction mixture was stirred at room temperature for 15 minutes. Acidification via acetic acid and dilution with water caused the formation of a precipitate. The crude product was filtered off and recrystallized from hexane to give 1.4 g. of the title compound—m.p. 230°–231° C.

Anal. calcd. for $C_{23}H_{19}N_3O_4$: C, 68.82; H, 4.77; N, 10.47. Found: C, 68.58; H, 4.83; N, 10.50.

Anti-secretory—60%

Anti-allergy—60%; 100 mg/kg i.p.

EXAMPLE 14

7,8-dihydro-5-hydroxy-8-(p-morpholinophenyl)-7-oxo-2-phenylpyrido[2,3-d]pyrimidine-6-carboxylic acid ethyl ester A mixture of 15 g. (0.057 mole) of 4-chloro-2-phenyl-5-pyrimidine carboxylic acid ethyl ester, 10.2 g. (0.057 mole) of p-morpholinoaniline and 3 g. (0.028 mole) of $Na_2CO_3$ in 400 ml. of ethanol was refluxed for 3 hours. Then the reaction solution was filtered and the filtrate immediately precipitated 4-(p-morpholinoanilino)-2-phenyl-5-pyrimidine carboxylic acid ethyl ester—m.p. 173°–176° C. No further purification was done and the product used directly in the next step.

Anal. calcd. for $C_{23}H_{24}N_4O_3$: C, 68.30; H, 5.98; N, 13.85. Found: C, 67.99; H, 6.10; N, 13.67.

100 ml. of 20% NaOH, 65 ml. of ethanol and 50 ml. of water were added to 17.6 g. (0.044 mole) of 4-(p-morpholinoanilino)-2-phenyl-5-pyrimidine carboxylic acid ethyl ester and refluxed 4 hours. The reaction mixture was cooled in ice and acidified with acetic acid. The deep orange solid was filtered off. The crude 4-(p-morpholinoanilino)-2-phenyl-5-pyrimidine carboxylic acid was triturated with 80% hot ethanol and then filtered. There was obtained 9.0 g. of bright yellow solid—m.p. 295° C. (dec.). The product was used in the next step without further purification.

Anal. calcd. for $C_{21}H_{20}N_4O_3$: C, 67.00; H, 5.36; N. 14.89. Found: C, 66.83; H, 5.18; N, 14.91.

30 ml. of xylene and 120 ml. of ethyl chloroformate were added to 12 g. (0.032 mole) of 4-(p-morpholinoanilino)-2-phenyl-5-pyrimidine carboxylic acid and refluxed 72 hours. Before the third night of reflux, an additional 100 ml. of ethyl chloroformate and 25 ml. of xylene were added to the reaction. At the end of 72 hours, the reaction was filtered. The product was collected on a suction filter and rinsed with petroleum ether to give 7 g. of 1-(p-morpholinophenyl)-7-phenyl-2H-pyrimido[4,5-d][1,3]oxazine-2,4(1H)-dione as a bright yellow product—m.p. 268° C. (dec.). This material was used directly in the next step without further purification.

50 ml. of NaOEt (0.8 g. Na–0.034 mole) was added to 5.45 g. (0.034 mole) of ethyl malonate and stirred 10 minutes at room temperature, then evaporated to dryness. Dimethylformamide was added until a solution was achieved and to this was added 6.95 g. (0.017 mole) of 1-(p-morpholinophenyl)-7-phenyl-2H-pyrimido[4,5-d][1,3]oxazine-2,4(1H)-dione and this mixture refluxed 1.5 hours. The chilled reaction was poured into dilute HCl and the resulting precipitate removed by filtration, rinsed with water and dried to give 6 g. of crude product. A sample of this was recrystallized from ethyl acetate to give a semi-hydrate compound with the m.p. 257° C. (dec.).

Anal. Calcd. for $C_{26}H_{24}N_4O_5 \cdot \frac{1}{2}H_2O$: C, 64.85; H, 5.23; N, 11.67. Found: C, 65.03; H, 5.49; N, 11.50.

EXAMPLE 15

7,8-dihydro-5-hydroxy-8-(4-methoxybenzyl)-7-oxo-2-phenylpyrido[2,3-d]pyrimidine-6-carboxylic acid ethyl ester A mixture of 11 g. (0.042 mole) of 4-chloro-2-phenyl-5-pyrimidine carboxylic acid ethyl ester, 5.7 g. (0.042 mole) of p-methoxybenzylamine and 2.2 g. (0.021 mole) of $Na_2CO_3$ in 250 ml. of ethanol was refluxed 3 hours. The reaction was then filtered and the filtrate chilled in ice. A precipitate formed and was filtered off giving 10.7 g. of 4-(p-methoxybenzylamino)-2-phenyl-5-pyrimidine carboxylic acid ethyl ester with m.p. 105°–110° C. This compound was used in the next step directly without further purification.

Anal. calcd. for $C_{21}H_{21}N_3O_3$: C, 69.40; H, 5.83; N, 11.56. Found: C, 68.82; H, 5.84; N, 11.50.

80 ml. of 20% NaOH and 10 ml. of ethanol were added to 10.7 g. (0.029 mole) of 4-(p-methoxybenzylamino)-2-phenyl-5-pyrimidine carboxylic acid ethyl ester and refluxed 3 hours. The reaction was cooled and acidified with dilute acetic acid and the ensuing white solid filtered off. Trituration with 95% ethanol yielded 8 g. of 4-(p-methoxybenzylamino)-2-phenyl-5-pyrimidine carboxylic acid—m.p. 263°-266° C. (dec.). This compound was used in the next step without further purification.

Anal. calcd. for $C_{19}H_{17}N_3O_3$: C, 68.05; H, 5.11; N, 12.53. Found: C, 67.61; H, 5.44; N, 12.69.

150 ml. of ethyl chloroformate and 30 ml. of xylene were added to 8 g. (0.024 mole) of 4-(4-methoxybenzylamino)-2-phenyl-5-pyrimidine carboxylic acid and refluxed 42 hours. The insoluble product was filtered and rinsed with petroleum ether to give 4.9 g. of 1-(4-methoxybenzyl)-7-phenyl-2H-pyrimido[4,5-d][1,3]oxazine-2,4(1H)-dione as a yellow solid—m.p. 248°-253° C. The product was used directly in the next step without further purification.

A 50 ml. solution of NaOEt was prepared (0.6 g. Na-0.028 mole) and 4.34 g. (0.028 mole) of ethyl malonate was added to it and stirred 10 minutes. Then this solution was stripped to dryness, dimethylformamide was added to the residue until a solution was again formed, and then 4.9 g. (0.014 mole) of 1-(4-methoxybenzyl)-7-phenyl-2H-pyrimido[4,5-d][1,3]oxazine-2,4(1H)-dione was added and heated to reflux for 1¼ hours. The reaction was then cooled and poured into dilute HCl. The white solid that formed was filtered off and rinsed with water and then with ethanol. Recrystallization from ethyl acetate gave 1.5 g. of the title compound with the m.p. 228°-232° C.

Anal. calcd. for $C_{24}H_{21}N_3O_5$: C, 66.81; H, 4.91; N, 9.74. Found: C, 66.60; H, 4.88; N, 9.63.

Anti-secretory—53%

Anti-allergy—78%; 25 mg/kg i.p.

EXAMPLE 16

7,8-dihydro-2,8-diphenyl-5-hydroxy-7-oxo-pyrido[2,3-d]pyrimidine-6-carboxylic acid ethyl ester A mixture of 10 g. (0.038 mole) of 4-chloro-2-phenyl-5-pyrimidine carboxylic acid ethyl ester and 7.1 g. (0.076 mole) of aniline in 200 ml. of ethanol was refluxed for 3 hours. Upon cooling a yellow solid precipitated from the solution. This was filtered off and rinsed with ethanol to give 4-anilino-2-phenyl-5-pyrimidine carboxylic acid ethyl ester, m.p. 98°-100° C. No further purification was done and the product was used directly in the next step.

Anal. calcd. for $C_{19}H_{17}N_3O_2$: C, 71.45; H, 5.37; N, 13.16. Found: C, 71.33; H, 5.27; N, 13.21.

60 ml. of 20% NaOH plus 20 ml. of ethanol were added to 10 g. (0.031 mole) of 4-anilino-2-phenyl-5-pyrimidine carboxylic acid ethyl ester and refluxed 3 hours. When cooled, a solid precipitate was obtained. The product was then slurried in water, acidified with acetic acid and filtered. Recrystallization from 95% EtOH gave 6.3 g. of 4-anilino-2-phenyl-5-pyrimidine carboxylic acid—m.p. 277°-280° C.

Anal. Calcd. for $C_{17}H_{13}N_3O_2$: C, 70.09; H, 4.50; N, 14.43. Found: C, 69.62; H, 4.86; N, 14.28.

100 ml. of ethyl chloroformate and 40 ml. of xylene were added to 6.3 g. (0.022 mole) of 4-anilino-2-phenyl-5-pyrimidine carboxylic acid and refluxed 27 hours. The insoluble material was removed by filtration and the filtrate was chilled in ice. The resulting solid was removed by filtration and rinsed with petroleum ether to give 1.2 g. of 1,7-diphenyl-2H-pyrimido[4,5-d][1,3]oxazine-2,4(1H)-dione—m.p. 252°-254° C. The material was used in the next step directly without further purification.

Anal. calcd. for $C_{18}H_{11}N_3O_3$: C, 68.13; H, 3.50; N, 13.24. Found: C, 68.40; H, 3.84; N, 13.26.

A 50 ml. solution of sodium ethoxide was prepared (0.2 g. Na-0.009 mole) and 1.5 g. (0.009 mole) of ethyl malonate was added to it and stirred 10 minutes. Then this solution was stripped to dryness, then dimethylformamide was added to the residue until a solution was formed and then 1.5 g. (0.005 mole) of 1,7-di-phenyl-2H-pyrimido[4,5-d][1,3]oxazine-2,4(1H)dione was added to this solution and heated to reflux for 2 hours. At the end of this time, the reaction was cooled and poured into dilute HCl. The white solid that formed was removed by filtration, rinsed with water and recrystallized from ethyl acetate to give 1.15 g. of the title compound with the m.p. 252° C. (dec.).

Anal. Calcd. for $C_{22}H_{17}N_3O_4$: C, 68.21; H, 4.42; N, 10.85. Found: C, 67.92; H, 4.24; N, 10.70.

Anti-secretory—64%

Anti-allergy—100%; 25 mg/kg i.p.

EXAMPLE 17

5-amino-7,8-dihydro-2-(methylphenylamino)-7-oxopyrido[2,3-d]pyrimidine-6-carboxylic acid ethyl ester Sodium (1.15 g.-0.05 g-atom) was dissolved in 350 ml. of ethanol and 9.3 g. (0.05 mole) of α-methyl-α-phenyl guanidine HCl was added to this solution and stirred 10 minutes. The reaction was filtered to removed NaCl and then 6.1 g. (0.05 mole) of ethoxymethylenemalononitrile was added to the filtrate and this mixture was refluxed for 3 hours. The reaction was chilled in ice and this caused the formation of a white solid—m.p. 188°-194° C. This crude material was recrystallized from ethanol to give 5.4 g. of solid 4-amino-2-(methylphenylamino)-5-pyrimidinecarbonitrile with m.p. 190°-195° C.

Anal. Calcd. for $C_{12}H_{11}N_5$: C, 63.98; H, 4.92; N, 31.09. Found: C, 63.89; H, 5.05; N, 31.10.

To 10 g. (0.044 moles) of 4-amino-2-(methylphenylamino)-5-pyrimidine-carbonitrile in 200 ml. of tetrahydrofuran was added 6.7 g. (0.044 moles) of ethyl malonyl chloride and then this mixture was heated at reflux for 2 hours. The reaction was then filtered and the filtercake rinsed with tetrahydrofuran. The filtrate was evaporated to dryness on a rotary evaporator. The viscous liquid residue was treated with 50 ml. of 20% NaOH and heated to boiling for 5 minutes. The resulting solid was removed by filtration. This solid was slurried in water, acidified with acetic acid and filtered. The crude product was recrystallized from 95% ethanol to give 1.05 g. of solid with m.p. 297° C. (dec).

Anal. calcd. for $C_{17}H_{17}N_5O_3$: C, 60.17; H, 5.05; N, 20.64. Found: C, 59.87; H, 4.93; N, 20.71.

Anti-secretory—25%

EXAMPLE 18

7,8-dihydro-5-hydroxy-8-methyl-2-(methylthio)-7-oxo-pyrido[2,3-d]pyrimidine-6-carboxylic acid ethyl ester To a mixture of 23.3 g. (0.1 mole) of 4-chloro-2-methylthio-5-pyrimidine carboxylic acid ethyl ester in 150 ml. of ethanol was added 15.5 g. (0.2 mole) of 40% aqueous methylamine. The mixture was stirred in an ice bath for 30 minutes and was filtered. The filter cake was recrystallized from ethanol to give 11 g. of 4- methylamino-2-methylthio-5-pyrimidine carboxylic acid ethyl ester—m.p. 87°–89° C. (Ref. E. Peters, et al., J. Org. Chem., 25, 2137 (1960)—m.p. 93°–94° C.).

To a solution of 4.54 g. (0.02 mole) of 4-methylamino2-methylthio-5-pyrimidine carboxylic acid ethyl ester in 100 ml. of anhydrous diethyl ether was added 1.5 g. (0.01 mole) of ethyl malonyl chloride. The mixture was stirred at room temperature for 1 hour. The mixture was filtered and the filtrate was evaporated in a rotary evaporator. The residue was triturated with a few ml. of diethyl ether and was filtered. The filtrate was evaporated and the residue was dissolved in 10 ml. of ethanol. This solution was added to a solution of 0.37 g. (0.015 g atom) of sodium in 20 ml. of ethanol. The mixture was stirred at room temperature for 10 minutes. The mixture was diluted with water and was acidified with glacial acetic acid. The precipitate which formed was collected, air dried and was recrystallized from ethanol to afford 0.4 g. of title product—m.p. 166°–168° C.

Anal. Calcd. for $C_{12}H_{13}N_3O_4S$: C, 48.80; H, 4.44; N, 14.23. Found: C, 48.60; H, 4.64; N, 13.89.

Anti-secretory—44%

Anti-allergy—100%; 10 mg/kg i.p.

EXAMPLE 19

7,8-dihydro-5-hydroxy-8-methyl-7-oxo-2-(1-pyrrolidinyl)pyrido[2,3-d]pyrimidine-6-carboxylic acid ethyl ester To a solution of 2.95 g. (0.01 mole) of 7,8-dihydro-5-hydroxy-8-methyl-2-(methylthio)-7-oxo-pyrido[2,3-d]pyrimidine-6-carboxylic acid ethyl ester (prepared by the method of Example 18) in 100 ml. of dichloromethane was added a suspension of 4.0 g. (0.02 mole) of 85% m—chloroperoxybenzoic acid in 50 ml. of dichloromethane. The mixture was stirred at room temperature for 1 hour. The solution was extracted with 100 ml. of a 20% potassium carbonate solution. The water layer was acidified with glacial acetic acid and was filtered. The filtrate was extracted with 50 ml. of chloroform. The chloroform layer was dried over magnesium sulfate, filtered and was evaporated in a rotary evaporator. The residue was recrystallized from ethanol to afford 1.0 g. of 7,8-dihydro-5-hydroxy-8-methyl-2-(methylsulfonyl)-7-oxo-pyrido[2,3-d]pyrimidine-6-carboxylic acid ethyl ester—m.p. 184°–185° C.

Anal. Calcd. for $C_{12}H_{13}N_3O_3S$: C, 44.03; H, 4.00; N, 12.84. Found: C, 44.41; H, 3.93; N, 12.72.

A stirred mixture of 3.27 g (0.01 mole) of 7,8-dihydro-5-hydroxy-8-methyl-2-(methylsulfonyl)-7-oxo-pyrido[2,3-d]pyrimidine-6-carboxylic acid ethyl ester and 0.71 g. (0.01 mole) of pyrrolidine in 50 ml. of ethanol was heated under reflux for 1 hour. The mixture was cooled and was filtered. The filter cake was recrystallized twice from ethyl acetate to afford 1.1 g. of title product—m.p. 174°–177° C.

Anal. Calcd. for $C_{15}H_{18}N_4O_4$: C, 56.59; H, 5.70; N, 17.60. Found: C, 56.63; H, 5.70; N, 17.55.

Anti-secretory—62%

Anti-allergy—96%; 10 mg/kg p.o.

EXAMPLE 20

7,8-dihydro-5-hydroxy-2-(methylthio)-7-oxo-8-propyl-pyrido[2,3-d]pyrimidine-6-carboxylic acid ethyl ester A stirred mixture of 23.3 g. (0.1 mole) of 4-chloro-2-methylthio-5-pyrimidine carboxylic acid ethyl ester, 5.9 g. (0.1 mole) of propylamine and 10.6 g. (0.1 mole) of sodium carbonate in 150 ml. of ethanol was heated under reflux for 5 hours. The mixture was filtered and the filtrate was evaporated in a rotary evaporator. The residue was triturated with 100 ml. of water and was extracted with 100 ml. of diethyl ether. The ether layer was dried over magnesium sulfate, filtered and was evaporated in a rotary evaporator to give about 13 g. of 2-methylthio-4-propylamino-5-pyrimidine carboxylic acid ethyl ester as an oil which was used directly in the next step without further purification. A small amount of this oil was dissolved in diethyl ether and was acidified with an ethereal hydrochloric acid solution. The precipitate which formed was collected and was recrystallized twice from ethyl acetate to afford the analytical sample, m.p. 132°–135° C.

Anal. Calcd. for $C_{11}H_{17}N_3O_2S \cdot HCl$: C, 45.28; H, 6.22; N, 14.40. Found: C, 45.05; H, 6.31; N, 14.35.

To a solution of 12.8 g. (0.05 mole) of 2-methylthio-4-propylamino-5-pyrimidine carboxylic acid ethyl ester in 100 ml. of anhydrous diethyl ether was added 0.75 g. (0.025 mole) of ethyl malonyl chloride. The mixture was stirred at room temperature for 4 hours and was filtered. The filtrate was evaporated in a rotary evaporator and the residue was dissolved in 15 ml. of ethanol and this solution was added to a solution of 1.15 g. (0.05 g atom) of sodium in 100 ml. of ethanol. After stirring at room temperature for 5 minutes, the mixture was diluted with water to the cloudy point and was acidified with conc. hydrochloric acid. The precipitate which formed was collected, air dried and was recrystallized from ethyl acetate to give 0.2 g. of title product—m.p. 130°–133° C.

Anal. Calcd. for $C_{14}H_{17}N_3O_4S$: C, 52.00; H, 5.30; N, 12.99. Found: C, 51.61; H, 5.32; N, 12.84.

Anti-secretory—69%

Anti-allergy—70%; 10 mg/kg i.p.

EXAMPLE 21

7,8-dihydro-5-hydroxy-8-isopropyl-2-(methylthio)-7-oxo-pyrido2,3-d]pyrimidine-6-carboxylic acid ethyl ester A stirred mixture of 23.26 g. (0.1 mole) of 4-chloro-2-methylthio-5-pyrimidine carboxylic acid ethyl ester and 11.82 g. (0.2 mole) of isopropyl amine in 200 ml. of ethanol was heated under reflux for 3 hours. The reaction mixture was taken to dryness on a rotary evaporator. The residue was triturated with water until a solid had formed. The solid product 2-methylthio-4-isopropylamino-5-pyrimidine carboxylic acid ethyl ester amounted to 28.1 g. An analytical sample was obtained by recrystallization from ethanol—$H_2O$ m.p. 42°–44° C.

Anal. calcd. for $C_{11}H_{17}N_3O_2S$: C, 51.74; H, 6.71; N, 16.46. Found: C, 51.52; H, 6.70; N, 16.53.

A mixture of 27.1 g. of 2-methylthio-4-isopropylamino-5-pyrimidine carboxylic acid ethyl ester, 100 ml. of water, 10 ml. of ethanol and 100 ml. of 50% sodium hydroxide solution was stirred at room temperature for 5 hours. The reaction mixture was filtered and the filtrate neutralized with glacial acetic acid. The 2-methylthio-4-isopropylamino-5-pyrimidine carboxylic acid which precipitated amounted to 15.5 g. An analytical sample was obtained by recrystallization from ethanol—m.p. 201°–203° C.

Anal. Calcd. for $C_9H_{13}N_3O_2S$: C, 47.56; H, 5.76; N, 18.49. Found: C, 47.41; H, 5.76; N, 18.70.

A stirred mixture of 14.0 g of 2-methylthio-4-isopropylamino-5-pyrimidine carboxylic acid, 100 ml. of ethyl chloroformate and 150 ml. of chloroform was heated for 24 hours under reflux. The solvents were removed in a rotary evaporator under suction. The IR spectrum of the residue indicates that cyclization to the anhydride had not occurred. Xylene (200 ml.) was added to the residue and the reaction mixture was heated under reflux for 3 hours. The reaction mixture was filtered and the filtrate taken to dryness on a rotary evaporator. The solid residue was washed with petroleum ether and amounted to 3.4 g. of 7-methylthio-1-isopropyl-2H-pyrimido[4,5-d][1,3]oxazine-2,4(1H)-dione—m.p. 94°-96° C. The product was used in the next step without further purification.

To a solution of sodium ethoxide (0.9 g. .039 g. atom of sodium in 75 ml. of ethanol) was added 6.24 g. (0.03 mole) of diethyl malonate. The ethanol was removed in a rotary evaporator. To the residue was added 100 ml. of dimethyl formamide followed by 3.3 g. (0.013 mole) of 7-methylthio-1-isopropyl-2H-pyrimido[4,5-d][1,3]oxazine-2,4(1H)-dione. The reaction mixture was heated under reflux for 1 hour, cooled in ice and poured into 400 ml. of water. The solution was acidified with conc. hydrochloric acid and the resulting product was collected by suction filtration. Recrystallization from ethanol gave 2 g. of product—m.p. 138°-140° C.

Anal. calcd. for $C_{14}H_{17}N_3O_4S$: C, 52.00; H, 5.30; N, 12.99. Found: C, 51.81; H, 5.56; N, 13.08.

Anti-allergy—84%; 25 mg/kg i.p.

EXAMPLE 22

7,8-dihydro-5-hydroxy-8-(2-methoxyethyl)-2-methylthio-7-oxopyrido-[2,3-d]pyrimidine-6-carboxylic acid ethyl ester A mixture of 11.63 g. (0.05 mole) of 4-chloro-2-methylthio-5-pyrimidine carboxylic acid ethyl ester and 7.51 g. (0.1 mole) of 2-methoxyethylamine in 100 ml. of ethanol was heated under reflux for 2 hours. The reaction mixture was filtered and the filtrate was taken to dryness on a rotary evaporator. The residue amounted to 11.9 g. of 2-methylthio-4-(2-methoxyethylamino)-5-pyrimidine carboxylic acid ethyl ester—m.p. 34°-35° C. Recrystallization from petroleum ether gave 8.9 g. of product, m.p. 36°-37° C.

Anal. Calcd. for $C_{11}H_{17}N_3O_3S$: C, 48.69; H, 6.31; N, 15.49. Found: C, 48.66; H, 6.40; N, 15.60.

To a mixture of 26.4 g. of 2-methylthio-4-(2-methoxyethyl)-5-pyrimidine carboxylic acid ethyl ester in 100 ml. of ethanol was added 100 ml. of water and 40 ml. of 50% sodium hydroxide solution. The reaction mixture was allowed to stir at room temperature for 2 hours and then acidified with glacial acetic acid. The resulting solid amounted to 18.0 g. of 2-methylthio-4-(2-methoxyethylamino)-5-pyrimidine carboxylic acid—m.p. 179°-185° C. The analytical sample was obtained by recrystallization from ethanol—m.p. 190°-192° C.

Anal. Calcd. for $C_9H_{13}N_3O_3S$: C, 44.23; H, 5.38; N, 17.27. Found: C, 44.35; H, 5.53; N, 17.47.

A mixture of 17 g. of 2-methylthio-4-(2-methoxyethylamino)-5-pyrimidine carboxylic acid and 100 ml. of ethyl chloroformate was heated under reflux for 5½ hours. The reaction mixture was taken to dryness on a rotary evaporator. The residue was recrystallized from ethanol giving 4.3 g. of 1-(2-methoxyethyl)-7-methylthio-2H-pyrimido[4,5-d][1,3]oxazine-2,4(1H)-dione—m.p. 134°-136° C.

Anal. Calcd. for $C_{10}H_{11}N_3O_4S$: C, 44.60; H, 4.12; N, 15.60. Found: C, 44.23; H, 4.33; N, 15.63.

To a solution of sodium ethoxide (1.1 g. 0.04 g. atom of sodium in 50 ml. of absolute ethanol) was added 7.69 g. (0.048 mole) of diethyl malonate. The ethanol was removed in a rotary evaporator. To the residue was added 50 ml. of dimethyl formamide followed by 4.4 g. (0.016 mole) of 1-(2-methoxyethyl)-7-methylthio-2H-pyrimido[4,5-d][1,3]oxazine-2,4(1H)-dione. The reaction mixture was heated under reflux for 1 hour, cooled in ice and poured into 400 ml. of water. Acidification with conc. hydrochloric acid gave 4.5 g. of product—m.p. 102°-104° C. Recrystallization from ethanol gave 3.9 g. of pure product—m.p. 110°-112° C.

Anal. Calcd. for $C_{14}H_{17}N_3O_5S$: C, 49.55; H, 5.05; N, 12.38. Found: C, 49.62; H, 5.24; N, 12.38.

Anti-secretory—47%

Anti-allergy—80%; 50 mg/kg p.o.

EXAMPLE 23

7,8-dihydro-5-hydroxy-2-(methylthio)-7-oxo-8-(2-propenyl)pyrido[2,3-d]pyrimidine-6-carboxylic acid ethyl ester To a suspension of 9.29 g. (0.04 mole) of 4-chloro-2-methylthio-5-pyrimidine carboxylic acid ethyl ester in 100 ml. of ethanol cooled in an ice bath was added 4.56 g. (0.08 mole) of allylamine dropwise over 5 minutes. The mixture was stirred at room temperature overnight. The ethanol was evaporated in a rotary evaporator and the residue was triturated with 50 ml. of ether and was filtered. The filtrate was evaporated and the residue was dissolved in ethanol and was diluted with water. The precipitate which formed was collected to give 3.8 g. of 4-allylamino-2-methylthio-5-pyrimidine carboxylic acid ethyl ester—m.p. 41°-43° C. (Ref. E. Peters et al., J. Org. Chem., 25, 2137 (1960); m.p. 44°-45° C.).

To a solution of 25.3 g. (0.1 mole) of 4-allylamino-2-methylthio-5-pyrimidine carboxylic acid ethyl ester in 400 ml. of anhydrous diethyl ether was added 7.5 g. (0.005 mole) of ethyl malonyl chloride. The mixture was stirred at room temperature for 3 hours. The mixture was filtered and the filtrate was evaporated in a rotary evaporator. The residue was dissolved in 15 ml. of ethanol and this solution was added to a solution of 2.3 g. (0.1 g. atom) of sodium in 200 ml. of ethanol. The mixture was stirred at room temperature for 5 minutes and was diluted with water, acidified with glacial acetic acid and was extracted with 150 ml. of diethyl ether. The ether layer was dried over magnesium sulfate, filtered and was acidified with gaseous hydrogen chloride. The mixture was filtered and the filtrate was cooled in ice. The precipitate which formed was collected and was recrystallized from ethyl acetate to give 0.2 g. of product—m.p. 134°-136° C.

Anal. Calcd. for $C_{14}H_{15}N_3O_4S$: C, 52.32; H, 4.71; N, 13.08. Found: C, 52.10; H, 4.76; N, 12.82.

Anti-secretory—48%

Anti-allergy—92%; 50 mg/kg p.o.

EXAMPLE 24

7,8-dihydro-5-hydroxy-2-methylthio-7-oxo-8-piperonyl pyrido[2,3-d]pyrimidine-6-carboxylic acid ethyl ester A mixture of 11.63 g. (0.05 mole) of 4-chloro-2-methylthio-5-pyrimidine carboxylic acid ethyl ester, 7.56 g. (0.05 mole) of piperonylamine and 5.3 g. (0.05 mole) of sodium carbonate in 100 ml. of ethanol was heated under reflux for 2 hours. The reaction mixture was cooled in ice, filtered and the filter cake washed with water to remove inorganic salts. The product 2-methylthio-4-piperonylamino-5-pyrimidine carboxylic acid ethyl ester amounted to 14.7 g.—m.p. 85°–88° C. It was used in the next step without purification.

Anal. Calcd. for $C_{16}H_{17}N_3O_4S$: C, 55.32; H, 4.93; N, 12.10. Found: C, 55.38; H, 4.88; N, 12.21.

To 100 ml. of 50% sodium hydroxide solution was added 14.7 g of 2-methylthio-4-piperonylamino-5-pyrimidine carboxylic acid ethyl ester. A few milliliters of ethanol was added. The reaction mixture was heated on a hot plate for a few minutes until a clear solution was obtained and then allowed to stir for several hours at room temperature. Acidification with conc. hydrochloric acid gave 13 g. of 2-methylthio-4-piperonylamino-5-pyrimidine carboxylic acid—m.p. 214°–217° C. The product was used in the next step without purification.

A mixture of 5 g. of 2-methylthio-4-piperonylamino-5-pyrimidine carboxylic acid in 50 ml. of ethyl chloroformate was heated under reflux for 2½ hours. The reaction mixture was cooled in ice and filtered under suction. The filter cake after washing with ethanol amounted to 4.0 g. of 7-methylthio-1-piperonyl-2H-pyrimido[4,5-d][1,3]oxazine-2,4(1H)-dione, hydrate—m.p. 160°–164° C. An analytical sample was obtained by recrystallizing from ethanol—m.p. 160°–162° C.

Anal. Calcd. for $C_{15}H_{11}N_3O_5S.H_2O$: C, 49.58; H, 3.60; N, 11.56. Found: C, 49.15; H, 3.49; N, 11.15.

To a solution of sodium ethoxide (1.6 g., 0.03 g. atom of sodium in 50 ml. of absolute ethanol) was added 4.8 g. (0.03 mole) of diethyl malonate. The ethanol was removed under suction in a rotary evaporator. To the residue was added 50 ml. of dry dimethyl formamide followed by 3.5 g. (0.01 mole) of 7-methylthio-1-piperonyl-2H-pyrimido[4,5-d][1,3]oxazine-2,4(1H)-dione. The reaction mixture was heated under reflux for 2 hours, cooled in ice and poured into 400 ml. of water. The reaction mixture was acidified with conc. hydrochloric acid. The resulting precipitateable amounted to 5.0 g.—m.p. 173°–178° C. Recrystallization from dimethyl formamide gave 3.4 g. of pure product—m.p. 187°–188° C.

Anal. Calcd. for $C_{19}H_{17}N_3O_6S$: C, 54.93; H, 4.12; N, 10.11. Found: C, 54.69; H, 4.27; N, 10.15.

Anti-secretory—47%

Anti-allergy—67.3%; 100 mg/kg i.p. 34.9%; 50 mg/kg p.o.

EXAMPLE 25

8-allyl-7,8-dihydro-5-(2-methoxyethylamino)-7-oxo-2-phenylpyrido[2,3-d]pyrimidine-6-carboxylic acid ethyl ester Twenty ml. of phosphorous oxychloride was combined with 0.87 g. (0.0025 mole) of 8-allyl-7,8-dihydro-5-hydroxy-7-oxo-2-phenylpyrido[2,3-d]pyrimidine-6-carboxylic acid ethyl ester and this was heated at reflux for 5 hours. Then the POCl₃ was evaporated and crushed ice added to the residue and the white solid that appeared was filtered off, rinsed with water and petroleum ether and dried to give 0.9 g. of 8-allyl-5-chloro-7,8-dihydro-7-oxo-2-phenylpyrido[2,3-d]pyrimidine-6-carboxylic acid ethyl ester—m.p. 148°–152° C. This product was used in the next step without further purification.

To 0.9 g. (0.0024 mole) of 8-allyl-5-chloro-7,8-dihydro-7-oxo-2-phenylpyrido[2,3-d]pyrimidine-6-carboxylic acid ethyl ester in 30 ml. of ethanol was added 0.17 g. (0.0024 mole) of 2-methoxyethylamine and 0.25 g. (0.0024 mole) of $Na_2CO_3$. This mixture was heated at reflux for 4 hours, then filtered and the filtrate chilled. Yellow crystals formed and were collected on a filter. Recrystallization from ethanol gave 0.5 g. of product—m.p. 155°–158° C.

Anal. Calcd. for $C_{22}H_{24}N_4O_4$: C, 64.69; H, 5.92; N, 13.72. Found: C, 64.43; H, 5.99; N, 13.47.

Anti-secretory—58%

EXAMPLE 26

7,8-dihydro-8-(2-methoxyethyl)-5-(2-methoxyethylamino)-7-oxo-2-phenylpyrido[2,3-d]pyrimidine-6-carboxylic acid ethyl ester 80 ml. of phosphorous oxychloride was combined with 4.0 g. (0.011 mole) of 7,8-dihydro-5-hydroxy-8-(2-methoxyethyl)-7-oxo-2-phenylpyrido[2,3-d]pyrimidine-6-carboxylic acid ethyl ester and heated at reflux for 5 hours. Then the POCl₃ was removed by evaporation and crushed ice added to the residue. The ensuing white solid was filtered off, rinsed well with water and petroleum ether and dried to give 3.8 g. of 5-chloro-7,8-dihydro-8-(2-methoxyethyl)-7-oxo-2-phenylpyrido[2,3-d]pyrimidine-6-carboxylic acid ethyl ester—m.p. 119°–121° C. This product was used in the next step without further purification.

To 2.4 g. (0.006 mole) of 5-chloro-7,8-dihydro-8-(2-methoxyethyl)-7-oxo-2-phenyl-pyrido[2,3-d]pyrimidine-6-carboxylic acid ethyl ester in 100 ml. of ethanol was added 0.45 g. (0.006 mole) of 2-methoxyethylamine and 0.65 g. (0.006 mole) of $Na_2CO_3$. This mixture was refluxed 3 hours, then filtered and the filtrate chilled. A solid formed and was filtered off and rinsed with petroleum ether—m.p. 160°–163° C. No further purification was necessary.

Anal. Calcd. for $C_{22}H_{26}N_4O_5$: C, 61.96; H, 6.15; N, 13.14. Found: C, 61.75; H, 6.09; N, 13.33.

Anti-secretory—12%

Anti-allergy—38%; 25 mg/kg p.o. 10 min. before antigen 2%; 25 mg/kg p.o. 60 min. before antigen

EXAMPLE 27

7,8-dihydro-8-ethyl-N-(2-hydroxyethyl)-5-(2-hydroxyethylamino)-7-oxo-2-phenylpyrido[2,3-d]pyrimidine-6-carboxamide To 2 g. (0.0056 mole) of 5-chloro-7,8-dihydro-8-ethyl-7-oxo-2-phenylpyrido[2,3-d]pyrimidine-6-carboxylic acid ethyl ester (prepared by the method of the first paragraph of Example 3) was added 20 ml. of 2-aminoethanol and this mixture was heated at reflux for 1.5 hours. The reaction mixture was chilled in ice and the product collected on a filter and recrystallized from ethanol to give 1.7 g. of product.—m.p. 250°–253° C.

Anal. Calcd. for $C_{20}H_{23}N_5O_6$: C, 59.84; H, 5.77; N, 17.45. Found: C, 59.95; H, 5.85; N, 17.34.

EXAMPLE 28

5-amino-7,8-dihydro-8-(2-methoxyethyl)-7-oxo-2-phenylpyrido[2,3-d]pyrimidine-6-carboxylic acid ethyl ester Combined 11 g. (0.051 mole) of 4-chloro-5-cyano-2-phenylpyrimidine, 5.4 g. (0.051 mole) of $Na_2CO_3$ and 3.8 g. (0.051 mole) of 2-methoxyethylamine in 250 ml. of ethanol and heated this at reflux for 3 hours. Then the reaction was filtered and the filtrate chilled. The product precipitated out of solution and was collected on a filter and rinsed with petroleum ether to give 9.3 g. of 4-(2-methoxyethylamino)-2-phenyl-5-pyrimidinecarbonitrile m.p. 122°–126° C. The product was used in the next without further purification.

To 9.3 g. (0.037 mole) of 5-cyano-4-(2-methoxyethylamino)-2-phenyl pyrimidine in 350 ml. of diethyl ether was added 2.8 g. (0.019 mole) of ethyl malonyl chloride and this mixture was stirred at room temperature for 4.5 hours. Then the solid material was filtered off and the filtrate evaporated to dryness. Ethanol was added until a solution was obtained and this solution was added to 0.85 g. (0.057 mole) of Na in ethanol and stirred 20 minutes. A little water was added and the solution was acidified with acetic acid. The solid product was collected on a suction filter and recrystallized from ethanol to give 2.0 g. of product—m.p. 245°–247° C.

Anal. Calcd. for $C_{19}H_{20}N_4O_4$: C, 61.94; H, 5.47; N, 15.21. Found: C, 61.59; H, 5.49; N, 15.31.

EXAMPLE 29

7,8-dihydro-5-hydroxy-N,8-bis(2-methoxyethyl)-7-oxo-2-phenylpyrido[2,3-d]pyrimidine-6-carboxamide To 1.0 g. (0.0027 mole) of 7,8-dihydro-5-hydroxy-8-(2-methoxyethyl)-7-oxo-2-phenylpyrido[2,3-d]pyrimidine-6-carboxylic acid ethyl ester (prepared as in Example 9) was added 0.4 g. (0.0054 mole) of 2-methoxyethylamine in 25 ml. of ethanol and this was heated at reflux for 4 hours. The reaction was then filtered and chilled and the filtrate gave up a solid that was collected on a suction filter and rinsed with petroleum ether. No further purification was necessary—m.p. 150°–154° C.

Anal. Calcd. for $C_{20}H_{22}N_4O_5$: C, 60.29; H, 5.57; N, 14.06. Found: C, 60.19; H, 5.72; N, 14.03.

EXAMPLE 30

N-[2-(diethylamino)ethyl]-7,8-dihydro-5-hydroxy-8-(2-methoxyethyl)-7-oxo-2-phenylpyrido[2,3-d]pyrimidine-6-carboxamide To 1.0 g. (0.0027 mole) of 7,8-dihydro-5-hydroxy-8-(2-methoxyethyl)-7-oxo-2-phenylpyrido[2,3-d]pyrimidine-6-carboxylic acid ethyl ester (prepared as in Example 9) was added to 0.63 g. (0.0054 mole) of diethylethylenediamine in 25 ml. of ethanol. This mixture was heated at reflux for 3.5 hours. Then ice-chilling caused the formation of a white solid that was filtered off and re-crystallized from ethanol to give 0.9 g. of product with a m.p. 115°–117° C.

Anal. Calcd. for $C_{23}H_{29}N_5O_4$: C, 62.85; H, 6.65; N, 15.94. Found: C, 62.91; H, 6.70; N, 15.84.

EXAMPLE 31

7,8-dihydro-5-hydroxy-7-oxo-2-phenyl-8-(2-propargyl)-pyrido[2,3-d]pyrimidine-6-carboxylic acid ethyl ester 10 grams (0.1 mole) of 95% propargylamine HCl was added to a solution of 2.4 g. (0.1 mole) of Na in 500 ml. of ethanol and stirred 15 minutes. Then the solid was filtered off and to the filtrate was added 27.3 g. (0.1 mole) of 4-chloro-2-phenyl-5-pyrimidinecarboxylic acid ethyl ester and 11 g. (0.1 mole) of $Na_2CO_3$. This mixture was heated at reflux for 3 hours. Then the reaction was again filtered and the filtrate chilled. The product precipitated out and was filtered off and rinsed with petroleum ether to give 25.8 g. of 2-phenyl-4-propargylamino-5-pyrimidinecarboxylic acid ethyl ester—m.p. 110°–115° C. The product was used in the subsequent step without further purification.

To 11.6 g. of 2-phenyl-4-propargylamino-5-pyrimidinecarboxylic acid ethyl ester in 200 ml. of ether and 800 ml. of tetrahydrofuran was added 3.1 g. (0.02 mole) of ethyl malonylchloride and this was stirred 2.5 hours at room temperature. Then filtration removed all solid and the filtrate was evaporated to dryness and ethanol was added to the residue. A solution of 0.95 g. (0.041 mole) of Na in 50 ml. of ethanol was added to the residue solution and stirred 10 minutes at room temperature. A little water was added and the solution acidified with acetic acid and the ensuing solid filtered off. Recrystallization from ethyl acetate gave 1.5 g. of product—m.p. 214°–215° C.

Anal. Calcd. for $C_{14}H_{15}N_3O_4$: C, 65.43; H, 4.33; N, 12.03. Found: C, 65.25; H, 4.56; N, 12.07.

Anti-allergy—68%; 25 mg/kg p.o. 10 min. before antigen 7%; 25 mg/kg p.o. 60 min. before antigen.

EXAMPLE 32

8-allyl-5-amino-7,8-dihydro-7-oxo-2-phenylpyrido[2,3-d]pyrimidine-6-carboxylic acid ethyl ester A mixture of 11.2 g. (0.052 mole) of 4-chloro-2-phenyl-5-pyrimidinecarbonitrile, 3.0 g. (0.052 mole) of allylamine and 5.5 g. (0.052 mole) of $Na_2CO_3$ in 250 ml. of ethanol was refluxed 4 hours. The solid material was then filtered off and the filtrate chilled. A solid precipitated out and was rinsed with petroleum ether to give 7.3 g. of 4-allylamino-2-phenyl-5-pyrimidinecarbonitrile—m.p. 158°–161° C. This material was used in a subsequent step without further purification.

Anal. Calcd. for $C_{14}H_{12}N_4$: C, 71.16; H, 5.12; N, 23.71. Found: C, 70.96; H, 5.11; N, 23.21.

A mixture of 7.3 g. (0.031 mole) of 4-allylamino-2-phenyl-5-pyrimidinecarbonitrile and 2.3 g. (0.015 mole) of ethyl malonyl chloride in 300 ml. of ether was stirred at room temperature for 4 hours. The reaction was then filtered and the filtrate evaporated to dryness. Ethanol was added to the residue and the slurry was then poured into a solution of 0.7 g. sodium (0.031 mole) in 50 ml. of ethanol and stirred for 20 minutes. Water was then added and the reaction acidified with acetic acid. The white solid was filtered off and recrystallized from ethanol to give 1.4 g. of product—m.p. 234°–236° C.

Anal. Calcd. for $C_{19}H_{18}N_4O_3$: C, 65.13; H, 5.18; N, 15.99. Found: C, 64.74; H, 5.07; N, 16.07.

What is claimed is:
1. A compound of the formula:

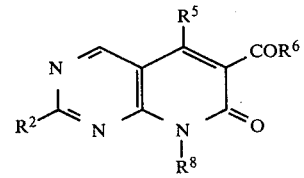

in which
R² is hydrogen, hydroxy, alkyl of 1 to 6 carbon atoms, alkylthio of 1 to 6 carbon atoms, phenyl, 4-methoxyphenyl, 4-chlorophenyl, 1-pyrrolidinyl or methylphenylamino;
R⁵ is hydroxy, alkylamino of 1 to 6 carbon atoms, 2-hydroxyethylamino, 2-alkoxyethylamino of 3 to 8 carbon atoms, dialkylamino wherein each alkyl group contains from 1 to 6 carbon atoms, 4-methyl-1-piperazinyl, 4-morpholinyl or 1-pyrrolidinyl when $R^2$ is other than alkylthio and $R^8$ is other than alkyl, or amino when $R^8$ is other than alkyl;

$R^6$ is amino, alkylamino of 1 to 6 carbon atoms or dialkylamino where each alkyl group contains from 1 to 6 carbon atoms and $R^8$ is hydrogen, alkyl of 1 to 6 carbon atoms, 2-alkoxyethyl of 3 to 6 carbon atoms, allyl, propargyl, phenyl, 4-methoxyphenyl, 4-chlorophenyl, benzyl, 4-methoxybenzyl, 4-chlorobenzyl, 4-(4-morpholinyl)-phenyl or piperonyl.

2. The compound of claim 1 in which $R^6$ is $-NH_2$.

3. The compound of claim 1 in which $R^6$ is alkylamino of 1 to 6 carbon atoms.

4. The compound of claim 1 in which $R^6$ is dialkylamino containing from 1 to 6 carbon atoms in each alkyl group.

* * * * *